United States Patent [19]

Pickering, Jr. et al.

[11] Patent Number: 4,996,381

[45] Date of Patent: Feb. 26, 1991

[54] INCREASED CONVERSION OF $C_2$–$C_{12}$ ALIPHATIC HYDROCARBONS TO AROMATIC HYDROCARBONS USING A HIGHLY PURIFIED RECYCLE STREAM

[75] Inventors: John L. Pickering, Jr., Kingswood, Tex.; Margaret Nemet-Mavrodin, Cherry Hill, N.J.

[73] Assignee: Mobil Oil Corp., New York, N.Y.

[21] Appl. No.: 254,556

[22] Filed: Oct. 7, 1988

[51] Int. Cl.$^5$ .............................................. C07C 15/00
[52] U.S. Cl. ...................................... 585/413; 585/415
[58] Field of Search ................................ 585/413, 415

[56] References Cited

U.S. PATENT DOCUMENTS

| | | | |
|---|---|---|---|
| 2,387,989 | 10/1945 | Foster | 585/413 |
| 2,394,170 | 2/1946 | Grosse et al. | 585/413 |
| 2,595,153 | 3/1951 | Layng | 585/413 |
| 3,756,942 | 9/1973 | Cattanach | 208/137 |
| 3,760,024 | 9/1973 | Cattanach | 260/673 |
| 3,845,150 | 10/1974 | Yan et al. | 260/673.5 |
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,167,472 | 9/1979 | Dick et al. | 585/413 |
| 4,180,689 | 12/1979 | Davies et al. | 585/401 |
| 4,211,640 | 7/1980 | Garwood et al. | 208/255 |
| 4,227,992 | 10/1980 | Garwood et al. | 208/46 |
| 4,229,602 | 10/1980 | Brinkmeyer et al. | 585/407 |
| 4,270,940 | 6/1981 | Rowles et al. | 62/28 |
| 4,350,835 | 9/1982 | Chester et al. | 585/417 |
| 4,519,825 | 5/1985 | Bernhard et al. | 62/28 |

OTHER PUBLICATIONS

S. DiCave et al., "Mathematical Model for Process Design and Dephlegmators (Partial Condensers for Binary Mixtures)", Canadian Journal of Chem. Eng., vol. 65, Aug. 1987, p. 559–564.

*Primary Examiner*—Patrick P. Garvin
*Assistant Examiner*—George R. Fourson
*Attorney, Agent, or Firm*—Alexander J. McKillop; Charles J. Speciale; Robert B. Furr, Jr.

[57] ABSTRACT

An improved aromatization process is disclosed in which conversion is increased by recycling a highly purified $C_2$–$C_4$ aliphatic stream. Loss of valuable ethane to fuel gas is substantially eliminated. In a preferred embodiment, a dephlegmator purifies the $C_2$–$C_4$ recycle stream.

8 Claims, 1 Drawing Sheet

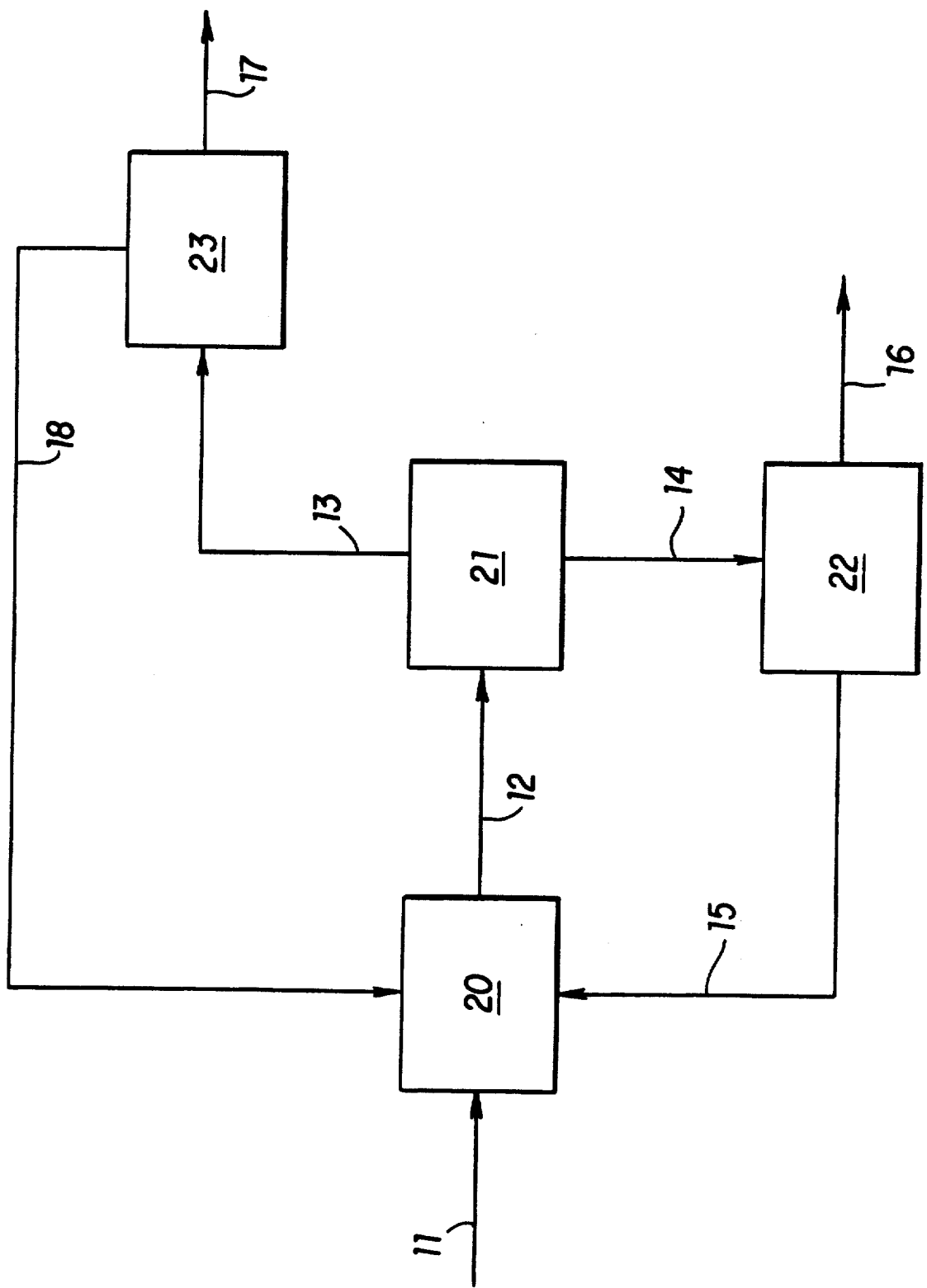

INCREASED CONVERSION OF $C_2$-$C_{12}$ ALIPHATIC HYDROCARBONS TO AROMATIC HYDROCARBONS USING A HIGHLY PURIFIED RECYCLE STREAM

FIELD OF THE INVENTION

This invention relates to the field of hydrocarbon upgrading processes. In particular, this invention relates to the aromatization of aliphatic hydrocarbons. More in particular, this invention relates to a method and apparatus for increasing the conversion of aliphatic hydrocarbons in a catalytic aromatization process.

BACKGROUND OF THE INVENTION

Developments in zeolite catalysis and hydrocarbon conversion processes have created interest in utilizing olefinic feedstocks for producing $C_5+$ gasoline, diesel fuel, etc. In addition to basic chemical reactions promoted by medium-pore zeolite catalysts, a number of discoveries have contributed to the development of new industrial processes. These are safe, environmentally acceptable processes for utilizing feedstocks that contain olefins. Conversion of $C_2$-$C_4$ alkenes and alkanes to produce aromatics-rich liquid hydrocarbon products were found by Cattanach (U.S. Pat. Nos. 3,760,024 and 3,756,942) and Yan et al. (U.S. Pat. No. 3,845,150) to be effective processes using medium-pore zeolite catalysts. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062; 4,211,640 and 4,227,992. Brinkmeyer et al. U.S. Pat. No. 4,229,602 teaches a dehydrocyclization process in which liquid and gas product streams are recycled to increase conversion to aromatics. The above-identified disclosures are incorporated herein by reference.

The product stream from a medium-pore zeolite catalyzed aromatization process contains hydrogen, uncoverted aliphatic feed, light aliphatic by-products, and aromatics. The $C_2+$ aliphatics may be recycled and aromatized. On the other hand, however, hydrogen and methane are not converted in the aromatization reaction and in fact hydrogen has been found to promote undesirable side reactions. Thus it has been discovered that it is highly desirable to remove hydrogen from the recycle stream.

The present invention provides an unexpected improvement in aromatics yield by removing substantially all of the hydrogen and methane from the recycle stream. Further, loss of valuable $C_2+$ aliphatics to fuel gas is essentially eliminated.

In particular, the invention increases conversion of aliphatics to aromatics by recycling both a $C_5+$ aliphatic stream and a highly purified $C_2$-$C_4$ aliphatic stream to the aromatization reactor. In a preferred embodiment, $C_2$-$C_4$ aliphatics are separated from hydrogen and methane in a dephlegmator process.

Dephlegmators are known in the art. For example, U.S. Pat. No. 4,270,940 to Rowles et al., incorporated herein by reference, teaches a process for the enhanced recovery of ethane and ethylene from demethanizer overhead by subjecting the uncondensed vapor effluent from the main reflux condenser to further condensation and accompanying rectification in a dephlegmator and returning the liquid condensate from the dephlegmator to the demethanizer column.

U.S. Pat. No. 4,519,825 to Bernhard et al. discloses a process for separating $C_4+$ hydrocarbons in high recovery and high purity from a light gas feedstream using a dephlegmator cycle.

A mathematical model of dephlegmation processes is described in DiCave, Mazzarrotta and Sebastiani, "Mathematical Model for Process Design and Simulation of Dephlegmators (Partial Condensers for Binary Mixtures)", 65 CANADIAN JOURNAL OF CHEMICAL ENGINEERING 559 (Aug., 1987).

For the purpose of this disclosure, the term "dephlegmation" is defined as a separation process as described above in which a refrigeration cycle is used to control partial condensation in a distillation process with countercurrent flow of rising vapor and falling condensate.

SUMMARY OF THE INVENTION

The present invention comprises a process and an apparatus for converting $C_2$-$C_{12}$ aliphatic hydrocarbons to aromatic hydrocarbons. A dephlegmator is used to purify a recycle stream and to increase the conversion of aliphatics to aromatics.

The process aspects of the invention comprise the steps of heating a feedstream comprising $C_2$-$C_{12}$ hydrocarbons, contacting said heated feedstream with a zeolite catalyst in a reaction zone under conversion conditions, withdrawing a product stream from said reaction zone, separating said product stream into a gas stream comprising hydrogen and $C_4-$ hydrocarbons and a liquid stream comprising aromatic hydrocarbons and $C_5+$ aliphatic hydrocarbons, further separating said liquid stream into an aromatic product and a heavy aliphatic recycle stream, mixing said heavy aliphatic recycle stream with said feedstream, further separating said gas stream into an off-gas stream comprising methane and hydrogen and a light aliphatic recycle stream, and mixing said light aliphatic recycle stream with said feedstream. The process may further comprise dephlegmating said gas stream into an off-gas stream and a light aliphatic recycle stream.

The apparatus aspects of the invention comprise means for heating a hydrocarbon feedstream, a reactor in communication with said heating means containing zeolite catalyst for converting said aliphatic hydrocarbon feedstream to a predominantly aromatic product stream, a gas-liquid separator in communication with said reactor for separating said product stream into a gas stream comprising hydrogen and $C_4-$ hydrocarbons and a liquid stream comprising aromatic hydrocarbons and $C_5+$ aliphatic hydrocarbons, an aromatic separator in communication with said gas-liquid separator for separating said liquid stream into an aromatic product stream and a heavy aliphatic recycle stream, a dephlegmator in communication with said gas-liquid separator for separating said gas stream into an off-gas stream comprising methane and hydrogen and a light aliphatic $C_2$-$C_4$ recycle stream, and mixing means in communication with said dephlegmator and said aromatic separator for combining said light aliphatic recycle stream and said heavy aliphatic recycle stream with said feedstream.

DESCRIPTION OF THE DRAWING

The FIGURE is a simplified schematic flow diagram of a preferred embodiment of the process of the present invention in which a dephlegmator is used to increase purity of the light aliphatic recycle stream.

DETAILED DESCRIPTION

Aromatization Process

Hydrocarbon upgrading reactions compatible with the process of the present invention include the conversion of aliphatic hydrocarbons to aromatic hydrocarbons. The following representative U.S. patents detail the feed compositions and process conditions for these reactions. Aromatization process conditions are summarized in Table 1.

U.S. Pat. No. 3,756,942, incorporated by reference as if set forth at length herein, discloses a process for the preparation of aromatic compounds in high yields which involves contacting a particular feed consisting essentially of mixtures of paraffins and/or olefins, and/or naphthenes with a crystalline aluminosilicate, e.g. ZSM-5, under conditions of temperature and space velocity such that a significant portion of the feed is converted directly into aromatic compounds.

U.S. Pat. No. 3,759,821, incorporated by reference as if set forth at length herein, discloses a process for upgrading catalytically cracked gasoline.

U.S. Pat. No. 3,760,024, incorporated by reference as if set forth at length herein, teaches a process for the preparation of aromatic compounds involving contacting a feed consisting essentially of $C_2$–$C_4$ paraffins and/or olefins with a crystalline aluminosilicate, e.g. ZSM-5.

U.S. Pat. No. 4,746,762 to Avidan et al., incorporated by reference as if set forth at length herein, teaches a process for upgrading an ethene-rich olefinic light gas to a liquid hydrocarbon rich in olefinic gasoline, isobutane and aromatics by catalytic conversion in a turbulent fluidized catalyst bed.

U.S. Pat. No. 4,751,338 to Tabak et al., incorporated by reference as if set forth at length herein, details the operation of a fluidized-bed aromatization reactor.

Hydrocarbon feedstocks which can be converted according to the present process include various refinery streams including coker gasoline, light FCC gasoline, $C_5$–$C_7$ fractions of straight run naphthas and pyrolysis gasoline, as well as raffinates from a hydrocarbon mixture which has had aromatics removed by a solvent extraction treatment. Examples of such solvent extraction treatments are described on pages 706–709 of the *Kirk-Othmer Encyclopedia of Chemical Technology*, Third Edition, Vol. 9, John Wiley and Sons, 1980. A particular hydrocarbon feedstock derived from such a solvent extraction treatment is a Udex raffinate. The paraffinic hydrocarbon feedstock suitable for use in the present process may comprise at least 75 percent by weight, e.g. at least 85 percent by weight, of paraffins having from 5 to 10 carbon atoms.

TABLE 1

| WHSV | |
|---|---|
| Broad range: | 0.3–300 hr$^{-1}$ |
| Preferred range: | 1–10 hr$^{-1}$ |
| OPERATING PRESSURE | |
| Broad: | 69–2170 kPa (10–315 psia) |
| Preferred: | 310–790 kPa (30–100 psig) |
| OPERATING TEMPERATURE | |

TABLE 1-continued

| Broad: | 540–820° C. (1000–1500° F.) |
|---|---|
| Preferred: | 560–620° C. (1050–1150° F.) |

The light aliphatic recycle stream preferably contains less than 2 wt. % hydrogen, more preferably less than 0.5 wt. % hydrogen. By minimizing this component in the recycle gas stream, undesirable side reactions are decreased thus increasing the aromatics yield.

Dephlegmation separates components boiling in a narrow range of temperatures into relatively pure effluent streams, thus providing a sharp cut point between components which are difficult and expensive to separate by other means, e.g. conventional distillation.

Catalysts

The members of the class of zeolites useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No.

4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are particularly preferred for use in the present invention and are disclosed in U.S. Pat. No. 4,350,835 and U.S. Pat. No. 4,686,312, both of which are incorporated by reference as if set forth at length herein.

Zinc-containing zeolite catalysts are useful in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Process Flow

In a preferred embodiment of the present invention, a $C_2-C_{12}$ aliphatic hydrocarbon stream is converted to a highly aromatic product stream. Referring to the Figure, a $C_2-C_{12}$ aliphatic hydrocarbon feedstream is charged through line 11 to an aromatization reactor 20 where it is converted to a reactor effluent stream consisting of aromatics, hydrogen, methane and heavier aliphatics. The aromatization reactor may comprise a fixed- or fluidized-bed reactor as described above. A moving-bed reactor may also be used. The reactor effluent stream flows through line 12 to gas-liquid separator 21 which consists of at least one separation stage. Depending on the feed composition and aromatization reaction zone conditions, more than one stage may be required. Thus separator 21 may comprise a flash drum, a plurality of flash drums, or a distillation tower. Hydrogen and $C_1-C_4$ aliphatics flow out of gas-liquid separator 21 through line 13 into dephlegmator 23. Liquid product consisting of aromatics and $C_5+$ aliphatics flows from gas-liquid separator 21 to aromatic separator 22 through line 14. Aromatic separator 22 typically employs a liquid-phase separation process as described above. One example of such a process is the Udex process. Aromatics are withdrawn from aromatic separator 22 through line 16, while $C_5+$ aliphatics are recycled to aromatization reactor 20 through line 15.

The stream of hydrogen and light aliphatic hydrocarbons charged to dephlegmator 23 is separated into an overhead gas stream containing methane and hydrogen and a light aliphatic recycle stream containing $C_2-C_4$ aliphatics. The light aliphatic recycle stream is charged to aromatization reactor 20 through line 18.

Dephlegmator 23 characteristically produces a sharp cut point between the overhead gas stream and the light aliphatic recycle stream. Most preferably, the overhead gas stream flowing through line 17 contains essentially no $C_2+$ material, while the light aliphatic recycle stream flowing through line 18 contains essentially no methane and hydrogen. As a result, the process economics are improved by converting a greater portion of the aliphatic feedstream to an aromatic product stream.

EXAMPLES

The following examples demonstrate the highly desirable product shift from light hydrocarbon off-gas to aromatics by recycling a highly purified $C_2-C_4$ aliphatic stream. In Examples 1 and 2, propane is charged to an aromatization reactor containing ZSM-5 under the following process conditions:

| Process Conditions | |
|---|---|
| Temperature | 565° C. (1100° F.) |
| Pressure | 170 kPa (10 psig) |
| WHSV | 1 hr$^{-1}$ |

Example No. 1 illustrates the conversion achieved in a conventional medium-pore zeolite catalyzed aromatization process with recycle of hydrogen and $C_1-C_3$ hydrocarbons. Example No. 2 shows increased conversion achieved with recycle of a $C_2-C_3$ aliphatic stream with essentially no hydrogen and methane. Process yields are shown in Table 1.

Table 2 compares fuel gas compositions for the two Examples showing a marked increase in methane burned as fuel gas and a decrease in valuable ethane burned as fuel gas.

TABLE 1

Process Yields From Propane Feed, Wt. %

| | Example No. 1 (Comparative) | Example No. 2 |
|---|---|---|
| Hydrogen | 6.5 | 8.6 |
| Benzene | 19.7 | 31.1 |
| | 57 | 61.5 |
| Toluene | 26.3 | 25.5 |
| $C_8$ Aromatics | 11 | 4.9 |
| $C_9+$ Aromatics | 6.5 | 8.3 |
| Fuel Gas | 33 | 21.6 |

TABLE 2

Fuel Gas Composition, Vol. %

| | Example No. 1 (Comparative) | Example No. 2 |
|---|---|---|
| Methane | 60 | 98 |
| Ethane | 40 | 2 |

We claim:

1. A process for converting an aliphatic $C_2-C_{12}$ hydrocarbon feedstream to a predominately aromatic product stream comprising the steps of:
   (a) heating a feedstream comprising $C_2-C_{12}$ hydrocarbons;
   (b) contacting said heated feedstream with a zeolite catalyst in a reaction zone under conversion conditions;
   (c) withdrawing a product stream from said reaction zone;
   (d) separating said product stream into a gas stream comprising hydrogen and $C_4-$ hydrocarbons and a liquid stream comprising aromatic hydrocarbons and $C_5+$ aliphatic hydrocarbons;
   (e) further separating said liquid stream of step (d) into an aromatic product and a heavy aliphatic recycle stream;
   (f) mixing said heavy aliphatic recycle stream with said feedstream of step (a);
   (g) further separating said gas stream of step (d) into an off-gas stream comprising methane and hydrogen and a light aliphatic recycle stream containing less than 0.5 wt. % hydrogen; and (h) mixing said light aliphatic recycle stream with said feedstream of step (a).

2. The process of claim 1 wherein said separating step (g) comprises dephlegmating said gas stream of step (d) into an off-gas stream and a light aliphatic recycle stream.

3. The process of claim 1 wherein said zeolite catalyst is a medium-pore zeolite catalyst having a Constraint Index of between 1 and about 12.

4. The process of claim 1 wherein said zeolite catalyst has the structure of one or more selected from the group consisting of ZSM-5, ZSM-11, ZSM-22, ZSM-23, ZSM-35 and ZSM-48.

5. The process of claim 1 wherein said zeolite catalyst has the structure of ZSM-5.

6. The process of claim 1 wherein said zeolite catalyst has the structure of Ga-ZSM-5.

7. The process of claim 1 wherein said conversion conditions comprise temperatures between 500° C. and 820° C., pressures between 170 kPa and 2170 kPa, and WHSV between 0.3 $hr^{-1}$ and 300 $hr^{-1}$, and wherein said light aliphatic recycle stream contains less than 0.5 wt. % hydrogen.

8. The process of claim 6 wherein said conversion conditions comprise temperatures between 520° C. and 650° C., pressures between 310 kPa and 790 kPa, and WHSV between 1 $hr^{-1}$ and 10 $hr^{-1}$.

* * * * *